United States Patent [19]

Dickens

[11] Patent Number: 4,589,287

[45] Date of Patent: May 20, 1986

[54] STRAIN GAUGE FOR MEDICAL PRESSURE MEASUREMENTS

[75] Inventor: Duane D. Dickens, San Clemente, Calif.

[73] Assignee: American Hospital Supply Corporation, Evanston, Ill.

[21] Appl. No.: 651,283

[22] Filed: Sep. 17, 1984

[51] Int. Cl.⁴ .............................................. G01L 9/06
[52] U.S. Cl. ..................................... 73/727; 128/675; 338/4; 338/42
[58] Field of Search ................. 73/726, 727, 720, 721; 338/4, 42; 128/675

[56] References Cited

U.S. PATENT DOCUMENTS 4,274,423  6/1981  Mizuno et al. ......................... 73/726
4,373,397  2/1983  Keller .................................... 73/727

Primary Examiner—Donald O. Woodiel
Attorney, Agent, or Firm—Weissenberger and Peterson

[57] ABSTRACT

A disposable strain gauge pressure sensor providing reliable electrical isolation even at defibrillation voltages in the measurement of biological fluid pressures is produced by floatingly mounting a glass plate on a closed cell, fluid-impervious foam pad within a firm but not totally rigid plastic housing. The glass plate has a thin glass diaphragm integrally formed therein which carries the strain gauge element. Openings in the foam pad and the housing allow a fluid contained in a fluid dome on the outside of the housing to bathe the side of the glass diaphragm opposite that on which the strain gauge element is mounted. The glass plate, foam pad, and housing are bonded together in fluid-tight relationship so that fluid cannot reach anything within the housing other than the glass diaphragm. The housing is preferably transparent to allow observation of the diaphragm during operation.

11 Claims, 4 Drawing Figures

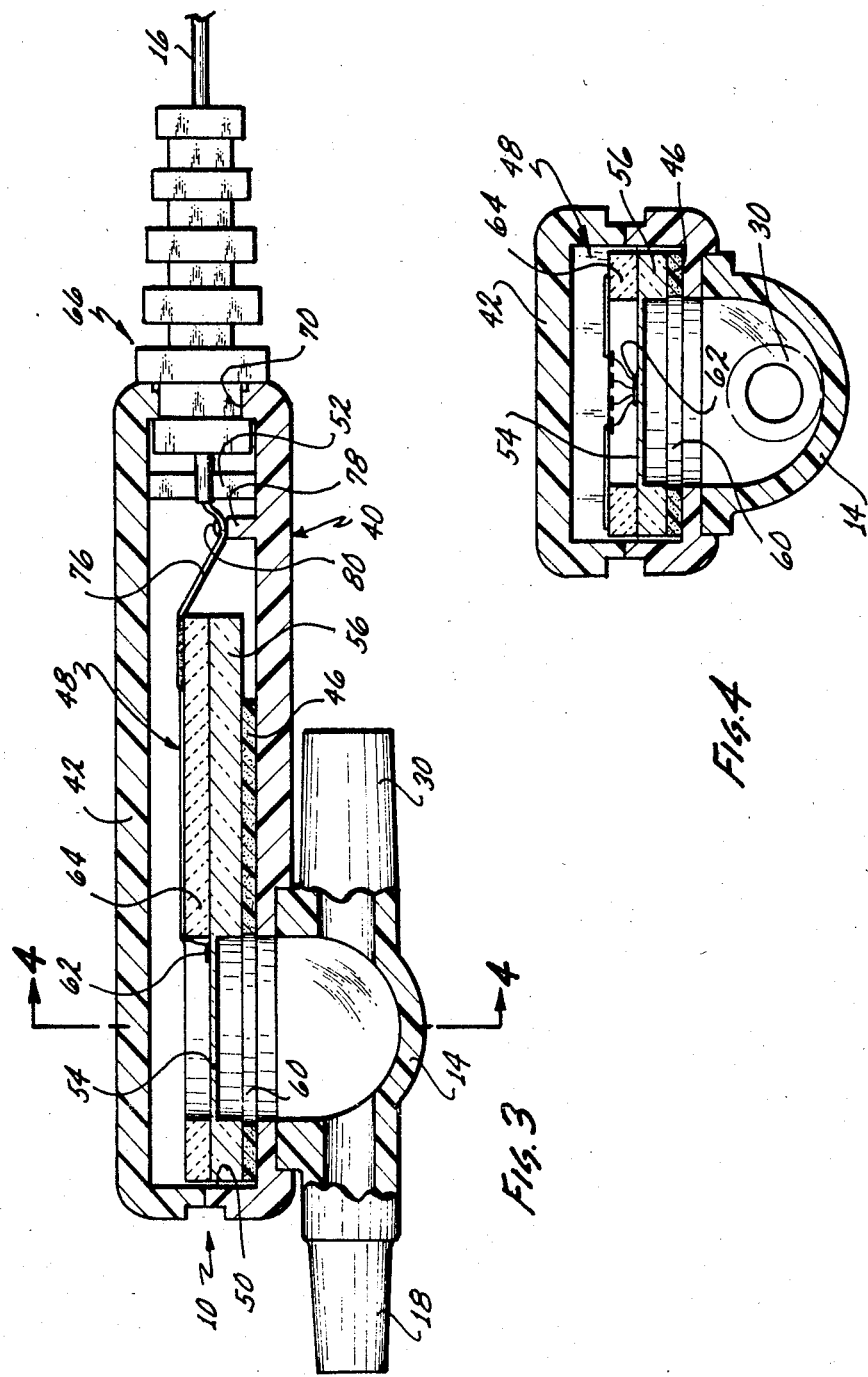

STRAIN GAUGE FOR MEDICAL PRESSURE MEASUREMENTS

This invention relates to pressure gauges of the strain gauge type, and more particularly to a disposable strain gauge for use in the measurement of biological fluid pressures.

BACKGROUND OF THE INVENTION

Strain gauges for the continuous monitoring of blood pressure, intracranial pressure, or the like in electric isolation from the patient even at the high voltages encountered in defibrillators which might be used on cardiac patients, have been well known for some time. Typically, prior art gauges of this type have had to be enclosed in an extremely rigid, relatively heavy housing of machined thermosetting materials or metals which would undergo no measurable deformation when handled by medical personnel. Because of their sturdy construction, such prior art gauges were expensive and did therefore not lend themselves to use as disposable sensing devices.

Some disposable prior art devices have been made, but these provided the electrical insulation needed between the measured fluid and a diffused silicon chip strain gauge by interposing a plug of silica gel between the fluid and the strain gauge. The silica gel would transmit the pressure of the fluid to the strain gauge but would prevent the formation of a ground path through the patient as long as the silica gel plus was properly in place. This arrangement limited the usefulness of prior art disposable gauges because it was possible for the silica gel to migrate and allow fluid to contact the strain gauge circuitry.

SUMMARY OF THE INVENTION

The present invention provides a simple, small medical pressure gauge of the strain gauge type which is impervious to handling, electrically safe, and yet inexpensive enough to be disposable. The invention achieves this result by floatingly suspending a strain gauge applied to a glass diaphragm on a closed cell foam pad mounted in a fluid-tight manner within a generally non-rigid enclosure. In the context of this discussion, the term "non-rigid" is used to designate materials which, though generally hard to the touch, have sufficient resiliency to undergo minute yet significant deformation when handled. The term "rigid" as used herein designates materials of sufficient hardness and rigidity to undergo no such deformation when handled.

The closed cell foam pad of this invention is bonded in a fluid-tight manner on one side to an interior support surface of the gauge's non-rigid housing, and on the other side to a glass plate in which a thin glass diaphragm is formed. A strain gauge is attached to the outer surface of the diaphragm and is connected to appropriate circuitry on a rigid circuit board bonded to the glass plate. The glass plate and circuit board together form the sensor plate of the gauge. An opening in the foam pad, and a corresponding opening in the support surface of the housing to which the foam pad is bonded, define a fluid-tight chamber which allows a fluid whose pressure is to be measured to bathe the inside of the glass diaphragm without allowing any fluid to reach any electrical parts of the strain gauge. The foam pad provides a mechanical damping effect which prevents slight deformations of the housing from being transmitted to the glass sensor plate.

It is therefor the object of this invention to provide an inexpensive strain gauge for medical applications which is impervious to handling and electrically safe, yet simple enough to be disposable. It is a further object of this invention to provide a strain gauge of the type described in which the gauge element is positioned on an insulating glass membrane floatingly supported on a foam pad in fluid-tight relationship to all electrical components of the gauge.

BRIEF DESCRIPTION OF THE DRAWINGS

FIG. 3 is a vertical section of the device of this invention in the longitudinal direction of the strain gauge.

FIG. 4 is a sectional view taken at right angles to the section of FIG. 3 through the center of the glass diaphragm.

BRIEF DESCRIPTION OF THE PREFERRED EMBODIMENT

Figures 1, 2:
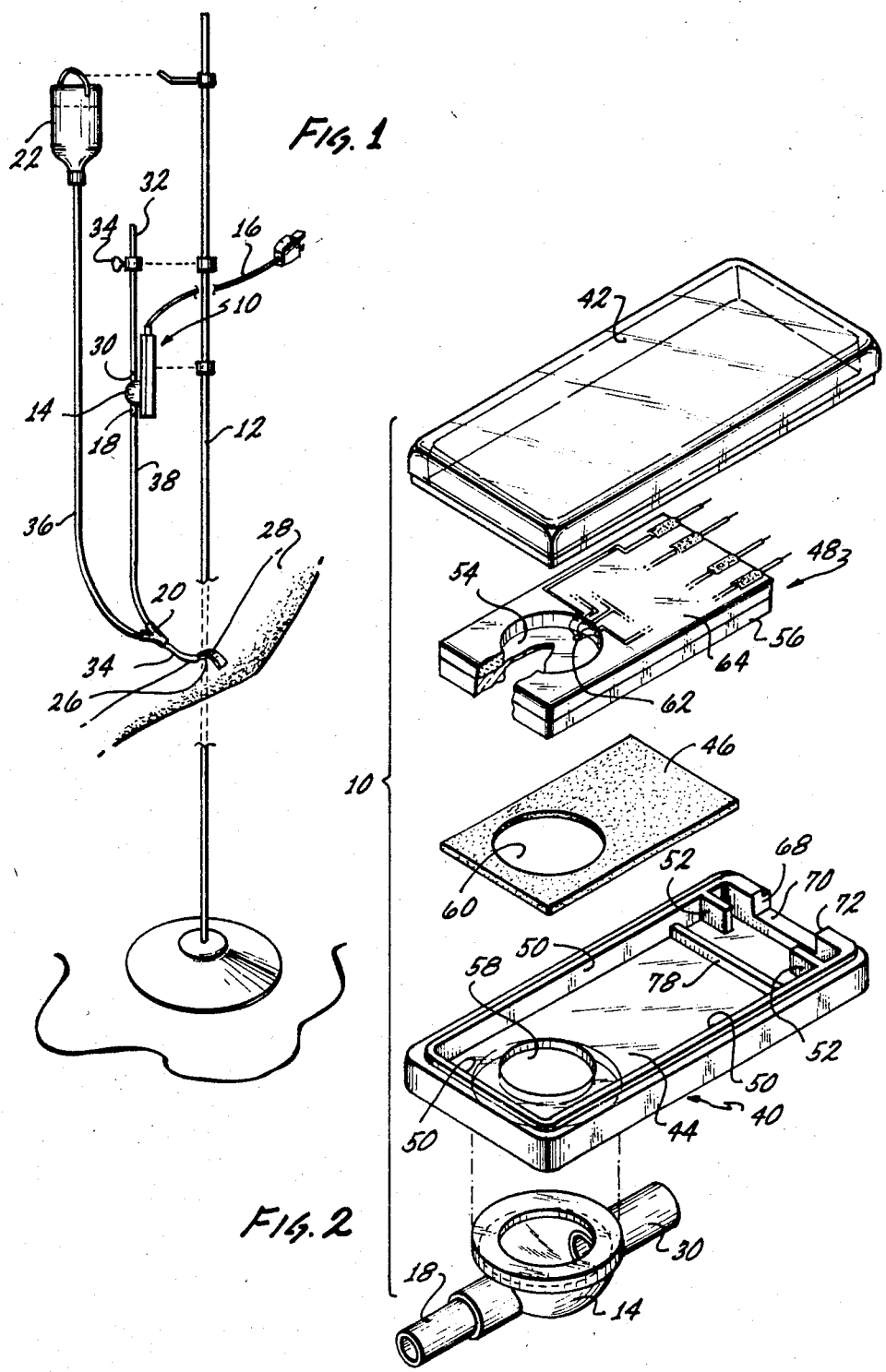
FIG. 1 is a partly schematic perspective view illustrating the manner in which the device of this invention may be used.
FIG. 2 is an exploded perspective view showing the various parts of the device of this invention.

FIG. 1 illustrates one of several ways in which the strain gauge 10 of the present invention may be advantageously used. The gauge 10 may be mounted on a stand 12 in a generally vertical attitude, with its fluid dome 14 located essentially at the mid-heart level of a patient whose blood pressure is to be continuously monitored. A cable 16 connects the gauge 10 to an appropriate external monitoring apparatus (not shown).

The fluid inlet 18 of the gauge 10 is connected to one branch of a Y fitting 20. The other branch of the fitting 20 is connected to a source 22 of saline solution which may contain heparin for antithrombogenic purposes. The stem of the Y fitting 20 is connected through an appropriate cannula 24 to a large diameter needle 26 which is inserted into an appropriate major blood vessel in a limb 28 of the patient. The fluid outlet 30 of the gauge 10 is connected to the open end of a tube 32 through a stopcock 34 mounted on the stand 12.

The stopcock 34 is initially opened to evacuate air forced out of the system by the saline solution from source 22 which fills conduits 36, 38 and the fluid dome 14 of gauge 10. Once all the entrapped air has been vented through open tube 32, stopcock 34 is closed. The head or pressure of the saline solution at source 22 is just sufficient to overcome the patient's blood pressure, so as to cause a slow continuous flow of saline solution into the patient's limb 28. In this manner, the patient suffers no blood loss, yet the pressure in the saline solution column in tube 38 and dome 14 is an accurate representation of the patient's blood pressure. It will be noted that in the system described, the fluid in the fluid dome 14 is essentially stationary during measurements, so that the measurement taken will correctly represent a static pressure unadulterated by flow-caused variations.

Turning now to FIG. 2, the gauge 10 will be seen to have a non-rigid housing 40, which together with the cover 42 forms a non-rigid fluid-tight enclosure when the housing 40 and cover 42 are solvent-bonded together. The housing 40 may preferably be molded from a biocompatible thermoplastic material such as polycarbonate. The thickness of the housing material may preferably be on the order of 0.2 mm. A housing of this type is inexpensive to fabricate but is subject to slight deformations when handled, even though it may feel hard to the touch. The sensitivity of the strain gauge of this invention is so great, however, that even this slight deformation could cause a false reading on the strain gauge if the sensor plate were directly mounted in the housing 40.

In accordance with the invention, the deformation problem is overcome by bonding to the support surface 44 of the housing 40 a resilient gasket in the form of a closed cell polyethylene foam pad 46 having a thickness within the range of about 0.5 mm to 1.3 mm and a density of about 6 to 30. The sensor plate 48 is then bonded to the other side of the foam pad 46 so as to be resiliently or floatingly supported thereby. The adhesive used to bond the pad 46 to the support surface 44 and sensor plate 48 may be an acrylic but is preferably natural rubber. Besides bonding, its primary purpose is to provide an effective and reliable fluid seal between the bonded parts.

It has been found that the thickness dimension of the foam pad 46 is limited at its lower end by its ability to properly isolate the sensor plate; i.e. an insufficient distance between the sensor and the housing would result in an undesirable mechanical coupling between them. The upper end of the thickness range of foam pad 46 is determined by excessive compliance of the pad 46, which destroys the frequency response of the sensor plate. The resonant frequency of the system should be on the order of 200 Hz.

The density of the foam is limited at its lower end by a mushy condition in which the sensor plate 48 can move appreciably with respect to the housing 40. At the upper end of the density range, the foam pad becomes dense enough to cause mechanical coupling to occur between the sensor plate and the housing. It is generally preferable to use densities at the lower end of the range for the foam pad 46 in order to minimize any mechanical coupling as much as possible.

With its thickness and density within the specified ranges, the foam pad 46 is capable of damping or absorbing and twisting stresses which may be introduced between the housing and the sensor plate 48 when the device is handled. It will be appreciated, as best shown in FIGS. 3 and 4, that the sensor plate 48 floats freely within the housing 40 on the foam pad 46 and does not touch the walls 50 or 52 of the housing 40.

The fluid receiving means of the inventive device (i.e. the fluid dome 14) is attached to the outside of the housing 40 and may typically be solvent-bonded thereto in fluid-tight relationship. The interior of the fluid dome 14 communicates with the inner surface of a thin glass diaphragm 54, formed in the glass plate portion 56 of sensor plate 48, through an opening 58 in the support surface 44 and an opening 60 in the foam pad 46. The inside of the fluid dome 14, together with the space defined by openings 58 and 60, forms a fluid-tight fluid chamber closed off by the glass diaphragm 54. In this manner, the entire glass diaphragm 54 is bathed by the fluid introduced into the fluid dome 14. For this purpose, and to prevent interference of the foam pad 46 with the flexing of diaphragm 54, the opening 60 in the foam pad 46 is made somewhat larger in diameter than the glass diaphragm 54 (e.g. about 10.1 mm as against about 9.5 mm).

The glass diaphragm 54 is formed integrally with the glass plate 56 and has a thickness on the order of 0.03 mm, as opposed to the roughly 0.2 mm thickness of the glass plate 56. The glass plate 46 is preferably formed of a heat-resistant, tempered glass such as Pyrex, whose coefficient of temperature expansion closely matches that of the silicon strain gauge element 62.

The glass diaphragm 54 has a high dielectric strength and therefore provides a highly adequate electrical insulation between the saline solution and the gauge circuitry even at the 8,000-odd volt level used in defibrillation equipment. The electric strain gauge element 62 is electrostatically bonded at a high temperature to the outer surface of the glass diaphragm 54. The element 62 is placed near the edge of the diaphragm 54, as that is the point of maximum stress. A ceramic wafer or circuit board 64 is bonded to the outside of the glass plate 56 to form, together with the glass plate 56, the sensor plate 48. Appropriate leads, connectors, and electronic circuit elements making up the compensation circuitry of the gauge are formed on the wafer 64 to electrically connect the strain gauge element 62 to the cable 16 in a conventional manner. Cable 16 is equipped with an integrally formed strain relief head 66 which is firmly held with respect to housing 40 in a conventional manner by a cable clamp formed by the housing surfaces 68, 70, 72 and the corresponding surfaces in the cover 42. The function of these clamp means engaging the strain relief head 66 is to prevent cable stresses from being transmitted to the sensor plate 48.

The housing 40 and cover 42, as well as the fluid dome 14, are preferably made transparent. This is desirable because for the proper functioning of the gauge 10, it is essential that there be no air bubbles trapped adjacent the glass diaphragm 54. The best way of achieving this result is for an operator to observe the diaphragm 54 through the housing 40 and cover 42 to ascertain that no bubbles are visible. The dome-like shape of fluid dome 14 is helpful in this respect by directing light from as many angles as possible against the glass diaphragm so as to facilitate its observation.

The end wall 52 of the housing 40 has a cutout 74 to allow wiring 76 to be brought from cable 16 to the circuit board 64. The wiring 76 is preferably bonded to a ridge 78 of the housing 40 by an epoxy bead 80 for additional security against stress transmission.

It will be seen that the foregoing construction results in a safe, sturdy, accurate yet disposable strain gauge for the continuous measurement of dynamic or static biological fluid pressures up to about 300 mmHg (with an overpressure capability to about 4,000 mmHg), as normally would be encountered in medical applications. Because of the imperviousness of the device to handling deformation, very substantial cost reductions can be achieved as opposed to the rigidly enclosed gauges of the prior art, without giving up any dielectric properties.

I claim:

1. A strain gauge for measuring the pressure of biological fluids, comprising:
   (a) a non-rigid housing including fluid receiving means, a generally planar support surface, and walls surrounding said support surface;
   (b) said support surface having an opening therein communicating with said fluid receiving means;
   (c) a closed cell foam pad secured in fluid-tight relationship to said support surface and having an opening therein communicating with said support surface opening; and
   (d) a sensor plate secured in fluid-tight relationship to said foam pad in spaced relation to said walls, said sensor plate having a glass diaphragm formed therewith, said glass diaphragm being in communication with said foam pad opening on one side thereof and having a strain gauge element applied thereto on the other side thereof.

2. The strain gauge of claim 1, in which said foam pad is positioned in spaced relationship to said walls.

3. The strain gauge of claim 1, in which said openings and fluid receiving means together define a fluid chamber to allow fluids in said fluid chamber to bathe said glass diaphragm.

4. The strain gauge of claim 1, further including:
(e) cable means for connecting said sensor means to external apparatus, said cable means having strain relief means integrally formed therewith;
(f) said housing including clamp means cooperating with said strain relief means to hold said cable means in a fixed position with respect to said housing.

5. The strain gauge of claim 4, in which said sensor plate further includes circuit board means bonded to said glass plate, said circuit board means being electrically connected to said strain gauge means and said cable means.

6. The strain gauge of claim 1, further comprising fluid inlet and outlet means associated with said fluid receiving means to fill said fluid receiving means with a fluid whose pressure is to be measured.

7. The strain gauge of claim 6, in which said fluid receiving means is a transparent fluid dome positioned on the outside of said housing in fluid-tight relationship to said outside of said housing, and adjacent said support surface opening for fluid communication therewith.

8. The strain gauge of claim 1, in which said foam pad opening is larger than said glass diaphragm.

9. The strain gauge of claim 1, in which said foam pad is on the order of 0.5 to 1.3 mm in thickness, and has a density on the order of 6 to 30.

10. The strain gauge of claim 1, in which said foam pad is about 0.8 mm thick and has a density of about 6.

11. The strain gauge of claim 1, in which said housing is transparent.

* * * * *